United States Patent [19]

Goebel et al.

[11] Patent Number: 4,608,818

[45] Date of Patent: Sep. 2, 1986

[54] MEDIUM-LOAD POWER-GENERATING PLANT WITH INTEGRATED COAL GASIFICATION PLANT

[75] Inventors: Konrad Goebel; Rainer Müller, both of Erlangen; Ulrich Schiffers, Eckental, all of Fed. Rep. of Germany

[73] Assignee: Kraftwerk Union Aktiengesellschaft, Mülheim/Ruhr, Fed. Rep. of Germany

[21] Appl. No.: 614,470

[22] Filed: May 25, 1984

[30] Foreign Application Priority Data

May 31, 1983 [DE] Fed. Rep. of Germany ....... 3319732

[51] Int. Cl.$^4$ ............................................. F02C 3/28
[52] U.S. Cl. ............................... 60/39.12; 60/39.182
[58] Field of Search .............. 60/39.07, 39.12, 39.465, 60/39.182; 518/702, 703

[56] References Cited

U.S. PATENT DOCUMENTS

| | | | |
|---|---|---|---|
| 2,401,845 | 6/1946 | Stephens | 137/568 |
| 3,183,666 | 5/1965 | Jackson . | |
| 3,244,106 | 4/1966 | Guy | 417/244 |
| 3,849,662 | 11/1974 | Blaskowski et al. | 60/39.182 |
| 3,868,817 | 3/1975 | Marion et al. . | |
| 3,904,386 | 9/1975 | Graboski et al. | 518/703 |
| 4,005,996 | 2/1977 | Hausberger et al. | 518/703 |
| 4,019,314 | 4/1977 | Springmann | 60/39.12 |
| 4,404,414 | 9/1983 | Penick et al. | 585/408 |

FOREIGN PATENT DOCUMENTS

| | | |
|---|---|---|
| 0038138 | 3/1981 | European Pat. Off. . |
| 0047596 | 8/1981 | European Pat. Off. . |
| 2807326 | 2/1978 | Fed. Rep. of Germany . |
| 3100751 | 7/1982 | Fed. Rep. of Germany . |
| 2075124 | of 1913 | United Kingdom . |
| 1167493 | 1/1967 | United Kingdom . |

OTHER PUBLICATIONS

ASME Paper, Title: Novel Gas Turbine Cycles with Coal Gasification, by S. Hamilton and S. J. Lehman.
Article from Dec. 1979 COMBUSTION—Title: The Integration of Gasification with Combined Cycle Power Plants, by R. W. Foster-Pegg, Westinghouse Electric Corp.

Primary Examiner—Louis J. Casaregola
Attorney, Agent, or Firm—Herbert L. Lerner; Laurence A. Greenberg

[57] ABSTRACT

Medium-load power generating plant with an integrated coal gasification plant, with a gas-turbine power generating plant part connected to the coal gasification plant, with a steam generating plant part connected to the raw-gas heat exchanger installation of the coal gasification plant, and with a methanol synthesis plant. The methanol synthesis plant has parallel-connected modules and is connected to the gas-turbine power generating plant part via a central purified gas distribution system which includes a purified gas continuous-flow interim storage plant connected parallel to the pure gas supply line and is connected on the gas side to the raw-gas heat exchanger installation.

16 Claims, 1 Drawing Figure

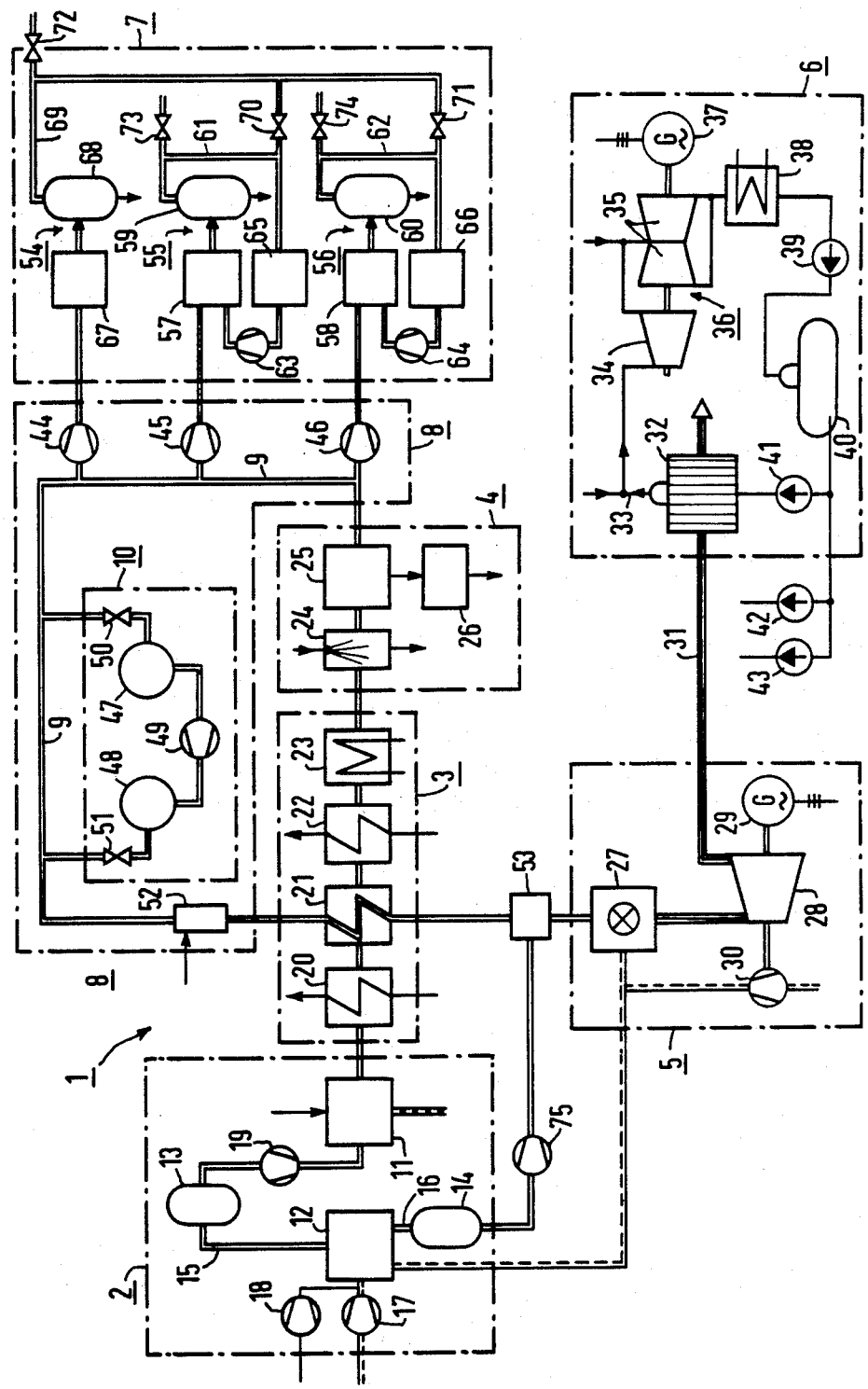

MEDIUM-LOAD POWER-GENERATING PLANT WITH INTEGRATED COAL GASIFICATION PLANT

BACKGROUND OF THE INVENTION

1. Field of the Invention

The invention relates to a medium-load power generating station with an integrated coal gasification plant, with a gas turbine power generating plant part connected to the coal gasification plant, with a steam power generating station part connected to the raw-gas heat exchanger system of the coal gasification plant, and with a methanol synthesis plant.

2. Description of the Prior Art

British Provisional Pat. No. 20 75 124 discloses a power generating plant, in which a gas turbine is supplied with purified gas from a coal gasification plant. The gas turbine drives an electric generator. The exhaust gas heat of the gas turbine is used in this power generating station for generating steam. The steam drives a steam turbine and a further electric generator. Provision is made in this power generating plant to feed part of the purified gas generated to a methanol synthesis plant and to store the methanol produced. The power output of this power generating station can be controlled synchronously with the output of the coal gasification plant. The output of the latter, however, can be controlled in the range of about 75 and 100%, and also with loss of efficiency at 55% of its rated power, if necessary. It is a peculiarity of this power generating station that load peaks are levelled out only by burning previously generated methanol in the gas turbine in addition to the purified gas. Shutting down the power generating station part which is coupled to the coal gasifier requires shutting down the methanol synthesis plant because there are no means for removal of heat from the raw gas.

European Pat. No. 00 38 138 describes a medium-load power generating plant which has two power generating plants which work completely independently of each other. Of these two power generating plants, the first power generating plant, which comprises a steam turbine plant connected to the waste-heat boiler of the gas turbine, is connected to a coal gasification plant. The coal gasification plant is also connected to a plant for generating synthetic fuels. The first power generating plant operates at base load and can be controlled only to the extent of the preceding coal gasification plant. The latter, however, can be controlled economically only in the range of 75 to 100% of its rated load. Its load behavior is determined decisively by that of the coal gasification plant including the air separation plant associated therewith. The second, independent power generating plant levels out the load fluctuations of the electric power production. In it, however, the substantially more expensive, previously generated synthetic fuel is burned. It is a peculiarity of this plant that excess purified gas must be burned off in the event of sudden load drop-off in the power generating station part, until the equilibrium between the production of purified gas the production of synthetic fuel at the new, lower power generating rate is reestablished. This energy loss can assume considerable proportions because regulating-down a larger coal gasification plant can take more than an hour, while the output of a gas turbine can be throttled down in a few minutes. When levelling-out load peaks as well as in the fast starting-up of this power generating plant, the relatively expensive previously generated fuel must be burned in the second independent power generating plant. This must be done until a power equilibrium is established again.

SUMMARY OF THE INVENTION

An object of the invention is to provide a medium-load power generating plant which does not require a further independent power generating system for intercepting load variations on the electric power side. This medium-load power generating plant will also handle peak load variations without using expensive secondary fuel. In addition, fuel loss in the event of sudden load reduction is prevented. Finally, the entire heat content of the gases produced in the medium-load power generating station is utilizable.

With the foregoing and other objects in view, there is provided in accordance with the invention a medium-load power generating plant with an integrated coal gasification plant comprising (a) a coal gasification plant for producing raw hot fuel gas containing carbon monoxide and hydrogen, (b) a raw gas heat exchanger installation having a first raw gas heat exchanger for indirect heat exchange between the hot raw gas from the coal gasification plant with feedwater to generate steam, (c) a gas purifier for purifying the raw gas, (d) a central purified gas distribution system, (e) a purified gas supply line connected to the raw gas heat exchanger installation and passing into the central purified gas distribution system, (f) a purified gas continuous-flow interim storage plant connected parallel to the purified gas supply line, (g) a gas turbine power generating plant connected to the coal gasification plant to receive fuel via the purified gas supply line, and (h) a methanol synthesis plant having parallel-connected modules for converting CO and $H_2$ into methanol connected to the gas turbine power generating plant via the central purified gas distribution system.

Other features which are considered as characteristic for the invention are set forth in the appended claims.

Although the invention is illustrated and described herein as embodied in a medium-load power-generating plant with integrated coal gasification plant, it is nevertheless not intended to be limited to the details shown, since various modifications may be made therein without departing from the spirit of the invention and within the scope and range of equivalents of the claims.

BRIEF DESCRIPTION OF THE DRAWING

The invention, however, together with additional objects and advantages thereof will be best understood from the following description when read in connection with the accompanying drawing which diagrammatically illustrates a medium-load power generating station in which are integrated a coal gasification plant wherein coal is gasified to produce raw fuel gas containing CO and $H_2$, a raw gas heat exchange plant wherein heat from the raw fuel gas is recovered and utilized to generate steam and to preheat purified fuel gas before being burned in the combustion chamber of the gas turbine, a gas purifier wherein the raw fuel gas is treated to remove impurities such as $H_2S$ and $SO_2$ and produce purified fuel gas, a steam power generating plant which utilized the heat from the gas turbine exhaust or the steam from the raw gas heat exchanger or both to run a steam turbine, a methanol synthesis plant divided into modules which is fed excess fuel gas for conversion into methanol, and a central purified gas distribution system which not only connects to the coal gasification plant and the methanol synthesis plant, but also contains an interim storage facility connected in parallel with the purified gas supply line—supplying or accepting purified fuel gas as needed. Thus, the coal gasification plant can be operated most efficiently and economically at a substantially constant output. Fluctuations in the demand for fuel gas by the gas turbine will be compensated by the interim storage facility. Larger changes in demand of fuel gas by the gas turbine in order to meet output requirements, can be met by cutting in or cutting out one or more modules of the methanol synthesis plant.

DETAILED DESCRIPTION OF THE INVENTION

In a medium-load power generating plant of the type mentioned at the outset, the methanol synthesis plant is therefore composed, according to the invention, of parallel-connected modules and is connected to the gas turbine power generating plant to a central purified gas distribution system which includes a purified gas continuous-flow interim storage facility connected in parallel to the purified gas supply line and follows on the gas side the raw gas heat exchanger system. In such medium-load power generating plant amounts of gas from the purified gas supply line in excess of that required is accumulated and stored in the interim storage facility until equilibrium between the generation and the demand of gas is reestablished. The equilibrium between gas production and consumption can be reestablished in steps in the event of decreasing or increasing power delivery to the network by connecting or disconnecting individual modules of the methanol synthesis. Larger or smaller amounts accumulated in the meantime can be taken up or given off by the continuous-flow purified interim accumulator connected to the purified gas supply line.

In a practical embodiment of the invention, the purified continuous-flow interim accumulator designed to keep the pressure in the purified gas supply line constant, acts as a control and interim-storage system. This is accomplished by means of a low-pressure and a high-pressure accumulator, which are connected to each other via a pressure-increasing compressor. Such a purified gas continuous-flow interim accumulator as a functional component of the central purified gas distribution system can, as a control and interim storage facility, keep the pressure in the purified gas supply line constant between two limits. Thereby, differences in the amount of gas generated and consumed are equalized automatically.

The utilization of the heat of the raw gas is improved if the raw-gas heat exchanger system comprises, according to the invention, three heat exchangers, of which the first and third serve for the generation of steam and the second for preheating the purified gas flowing into the combustion chamber of the gas turbine of the gas turbine power generating plant part. High-pressure steam fed into the high-pressure part of the steam turbine can be generated in the first heat exchanger. Low-pressure steam generated in the third heat exchanger, can be fed into the low-pressure part of the steam turbine, and can also be used as process steam The flexibility of the medium-load power generating plant is increased if the capacity of the first and the third heat exchanger is sufficient, with the gas turbine shut down and the coal gasification plant running, to drive the gas turbine for maintaining the internal electric power requirements of the coal supply system and the methanol synthesis plant.

The third heat exchanger desirably has adequate heating surfaces to absorb the additional raw gas heat additionally produced if the gas turbine is only partially loaded or is shut down. With the gas turbine shut down, the raw gas which flows into the third heat exchanger is at a higher temperature and generates a larger quantity of steam. The latter can thus substitute at least partially, for the amount of steam which is missing from the waste heat boiler.

The adaptability of the medium-load power generating plant to different load states is increased especially in the lower load range if, in a practical embodiment of the invention, the not completely reacted synthesis exhaust gas can be returned in at least one of the modules of the methanol synthesis plant by means of a recirculating compressor via a hydrogen enrichment stage to the synthesis reactor. The hydrogen and carbon monoxide content of the purified gas fed to these modules at low load can thereby be more completely reacted.

The methanol synthesis plant can be simplified if, in a particularly practical further embodiment of the invention, the not completely reacted exhaust gas of at least one module of the methanol synthesis plant is fed via a mixing section into the purified gas supply line leading to the gas turbine power generating plant part. Several advantages are achieved immediately by this arrangement of at least one module of the methanol synthesis plant. Because this module is designed as a continuous-flow synthesis module, i.e. without recirculation compressor and without hydrogen enrichment stage, its capital and energy costs are lower than in modules in which the synthesis gas is recirculated. Consequently, the methanol can be produced more cheaply here. In addition, the synthesis gases of this module of the methanol synthesis plant have a sufficiently high calorific value so that they can be fed via a mixing section into the purified gas supply line leading to the gas-turbine power generating plant part. This has the further benefit that this module remains in operation in all operating states of the medium-load power generating station, so that the amount of gas fed into the purified supply line is approximately constant and substitutes for a corresponding share of purified gas.

Thus, in a practical further embodiment of the invention, the not fully reacted synthesis exhaust gas of at lest one module of the methanol synthesis plant can be fed into the recirculation line returning to the synthesis reactor of one of the other modules for the accelerated start-up of the synthesis reactor thereof. In the event of a rapidly increasing supply of purified gas, such as, for instance, when the gas turbine is shut down, load shedding etc., further modules of the methanol synthesis plant can be heated up rapidly by feeding the not completely reacted hot synthesis exhaust gas of a module in operation, and can therefore be put in operation in substantially shorter time. Thereby, the requirements as to the storage capacity of the purified gas continuous-flow interim storage plant are reduced.

Further details of the invention will be explained with the aid of an embodiment example.

The drawing is a schematic presentation of a medium-load power generating station according to the invention.

The most important subassemblies of the medium-load power generating station 1 according to the invention shown in the embodiment example are a coal gasification plant 2, a raw-gas heat exchanger plant 3, a gas purifier 4, a combination power generating plant consisting of a gas turbine power generating plant part 5 and a steam power generating plant part 6, a methanol synthesis plant 7 and a central purified-gas distribution system 8 with a pure-gas continuous-flow interim storage facility 10 which is connected parallel to the purified gas supply line 9. The coal gasifier system 2 contains a coal gasifier 11, and air separation plant 12, one buffer accumulator 13, 14 each in the oxygen line 15 and the nitrogen line 16 of the air separation plant 12, two additional air compressors 17, 18 connected in series with the air separation plant, and one further gas compressor 19 arranged in the oxygen line 15 leading to the coal gasifier 11. The raw gas heat exchanger installation 3 arranged in the gas stream of the coal gasifier comprises a first heat exchanger 20 for generating steam, a second raw gas/purified gas heat exchanger 21 for preheating the purified gas, and a third heat exchanger 22 likewise for generating steam. Finally, a regulating cooler 23 is further provided in the raw-gas heat exchanger installation 3. The gas purifier 4 following the raw gas heat exchanger installation 3 comprises a raw gas scrubber 24, a hydrogen sulfide absorption facility 25 and a sulfur extraction plant 26.

A gas-turbine power generating plant part 5 is connected to the purified gas supply line leaving the raw gas/purified gas heat exchanger 21. In the embodiment example it comprises only one combustion chamber 27, a gas turbine 28 and one each generator 29 and air compressor 30 driven by the gas turbine. A waste heat boiler 32 is provided at the exhaust gas line 31 leaving the gas turbine. Boiler 32 is connected to the steam line 33 which is connected to a steam turbine 36 of the steam power generating station 6, consisting of a high-pressure part 34 and a low-pressure part 35. The steam turbine drives a generator 37. The low-pressure part 35 of the steam turbine 36 is followed by a condenser 38, a condensate pump 39, a feedwater tank 40 as well as by several feedwater pumps 41, 42, 43.

In addition to the purified gas supply line 9 and the purified gas continuous-flow interim accumulator 10, the central purified-gas distribution system 10 also includes the purified gas compressors 44, 45, 46 supplying the methanol synthesis plant 7. The purified gas continuous-flow interim accumulator 10 contains a low-pressure accumulator 47 and a high-pressure accumulator 48 and an interposed purified gas compressor 49. The low-pressure accumulator 47 is connected via a charging valve 50 and the high-pressure accumulator 48 via a discharge valve 51 to the purified gas supply line 9. If the pressure in the purified gas supply line 9 drops below a preset value, the discharge valve 51 is opened via pressure sensors, not shown, in known manner. The charging valve 50 is controlled to open if the pressure in the purified supply line 9 rises above a preset value. A mixing section 52 for admixing synthesis gas from the methanol synthesis plant 7 is provided in the purified-gas supply line 9 leading to the raw gas/purified gas preheater 21. A mixing chamber 53 for admixing nitrogen to the purified gas is further provided immediately ahead of the combustion chamber 27 of the gas turbine 28.

In the embodiment example, the methanol synthesis plant 7 consists of three parallel-connected modules 54, 55, 56, of which two modules 55, 56 consist of a synthesis reactor 57, 58; a methanol separator 59, 60; a recirculation line 61, 62 which returns the synthesis exhaust gases of the methanol separator to the synthesis reactor with a loop compressor 63, 64; and of a hydrogen enrichment stage 65, 66. A further module 54 of the methanol synthesis plant 7 is equipped with only one synthesis reactor 67 and a methanol separator 68 following the former. Its synthesis exhaust gas line 69 is connected via valves 70, 71, 72 to the recirculating lines 61, 62 of the remaining modules 55, 56 and to the mixing section 52 in the purified gas supply line 9.

In nominal-load operation, the air separation plant 12 is supplied with compressed air by the air compressor 30 driven by the gas turbine 28 as well as by at least one of the supplemental air compressors 17, 18 of the air separation plant. The oxygen of the air separation plant is injected via the buffer accumulator 13 and the gas compressor 19 into the coal gasifier 11. The coal in the coal gasifier is gasified with the oxygen and process steam fed-in into the coal gasifier to form raw gas. The raw gas which has a temperature of 800 to 1600° C. gives up, first, part of its heat in the first heat exchanger 20 of the raw gas heat exchanger installation 3. High-pressure steam for feeding into the high-pressure part 34 of the steam turbine 36 is generated in raw gas heat exchanger plant 3. The purified gas flowing to the combustion chamber 27 of the gas turbine 28 is preheated by the waste heat of the raw gas in the second heat exchanger 21 of the raw gas heat exchanger installation. Further heat is removed from the purified gas in the third heat exchanger 22, in which low-pressure steam is generated. This low-pressure steam is fed, in nominal-load operation, partly into the low-pressure part 35 of the steam turbine 36 and is used partly as process steam and, for instance, is introduced into the coal gasifier 11. The raw gas temperature is regulated to a predetermined temperature in the regulating cooler 23 following the third heat exchanger 22 of the raw-gas heat exchanger installation before it enters the gas purification plant 4 connected thereto. The raw gas flowing through the gas purification plant 4 is first purified of dust particles in the raw-gas scrubber 24 and in the following hydrogen sulfide absorption plant 25 of hydrogen sulfide. The hydrogen sulfide-containing exhaust gas of the hydrogen sulfide absorption plant 25 is converted into sulfur in the sulfur extraction plant 26. The purified gas leaving the gas purification plant 4 is fed via the purified gas supply line 9 to the purified gas continuous-flow interim storage plant 10 as well as to the other gas consumers. The purified gas is compressed by the purified gas compressors 44, 45, 46 to synthesis pressure in the operative modules of the methanol synthesis plant 7 and fed to the respective methanol synthesis reactor. In nominal-loss operation, preferably only module 54 which is run in continuous-flow operation, is operative. Its synthesis gas leaving the methanol synthesis reactor 67 is freed of the methanol in the methanol separator 68 connected thereto. The synthesis exhaust gas flowing from the methanol separator 68 is only partially reacted and therefore still has a calorific value which differs not too greatly from the calorific value of the purified gas. The accumulating synthesis exhaust gas can be fed via the mixing section 52 into the purified gas line leading to the combustion chamber 27 of the gas turbine. There, it substitutes for part of the purified gas.

The other two modules 55, 56, each provided with a recirculating line 61, 62 are switched into the circuit if an excess of purified gas is available, as for example in the event, the power output of the gas turbine 28 was reduced and this amount of pure gas cannot be picked up by speeding up the already operative module 54. In the circuits of modules 55, 56, the synthesis exhaust gas is returned, via the recirculating line 61, 62 and a hydrogen enrichment stage 65, 66, into the methanol synthesis reactor 57, 58. In the hydrogen enrichment stage, the stoichiometric ratio of $H_2$ to $CO=2$ required for the methanol synthesis is re-established by the addition of hydrogen. The hydrogen enrichment stages could also be built into the purified gas lines to the synthesis reactors instead of the recirculating lines. Through recirculation of the synthesis exhaust gases, the hydrogen and carbon monoxide components can be reacted almost completely. To prevent build-up of inert gases in the recirculating synthesis exhaust gas, small amounts of the synthesis exhaust gas can be drained off as residual gas via the valves 73, 74 and are burned in a steam generator, not shown here in detail. Its steam can be used as process steam or as steam for operating a separate steam turbine.

Alternatively, this residual gas can also be burned in a separate gas turbine. By this steam turbine or gas turbine together with a generator, electric energy can be generated adequate for covering the internal requirement of the medium-load power generating plant 1.

The gas turbine 28 drives the generator 29 and the air compressor 30. It supplies the combustion chamber 27 of the gas turbine as well as the air separation plant 12 with compressed air. Because the output of the air compressor 30 is matched to the amount of air required by the gas turbine at full load, a controlled supplemental air compressor 17 must be operative for covering the overall oxygen requirement of the coal gasification plant 2 at full load of the gas turbine power generating station part 5 and during the operation of the module 52 of the methanol synthesis plant. This supplementary air compressor 17 as well as further parallel-connected supplementary air compressors furnish the amount of air required for the gasifier 11 to continue to operate the methanol synthesis system 7 while the gas turbine 28 is at constant power output.

To reduce the formation of $NO_x$ in the combustion of the pure gas, nitrogen from the air decomposition plant 12 is admixed to the pure gas by means of a compressor 75 before it enters the combustion chamber 27. This causes a lower flame temperature and thereby, the $NO_x$ production is decreased. The admixed amount of nitrogen is adapted to the capacity of the gas turbine at the condition of operation. Excess nitrogen, which cannot be taken up by the gas turbine, can be intercepted in the buffer accumulator 14. If less purified gas is fed to the gas turbine at reduced load, more nitrogen can be admixed within certain limits. The hot exhaust gases of the gas turbine 28 are conducted via the exhaust gas line 31 into the waste heat boiler 32. Its exhaust heat is used to generate steam. The steam generated in the waste heat boiler as well as steam additionally generated in the raw gas heat exchanger plant 3 are fed to the steam turbine 36. The steam leaving the low-pressure part 35 of the steam turbine is condensed in the condenser 38. The condensate is pumped into the feedwater tank 40. The water can then be transported back via the feedwater pumps 41, 42, 43 into the waste heat boiler and the other heat exchangers 20, 22.

If the drive power of the gas turbine 28 is reduced, the purified gas throughput through the purified gas/raw gas heat exchanger 21 is also decreased. This leads to a higher input temperature of the raw gas into the third heat exchanger 22. The latter however, is laid out and designed so that it can take up the increased heat supply of raw gas even if the gas turbine is completely shut off and there is no raw gas cooling in the raw gas/purified gas heat exchanger 21. A correspondingly larger amount of steam is produced by adaptation of the feedwater feed. This result is obtained by feeding the feedwater to the low-pressure part 35 of the steam turbine 36 and compensated in part for the lower steam supply of the waste heat boiler 32 of the gas turbine 28. Due to the reduction of the gas turbine power output, the constant gas supply of the coal gasifier plant 11 is faced with a reduction in gas consumption. This leads to an increase of the pressure in the purified gas supply line 9 beyond a preset reference pressure and thus, to activation of the charging valve 50 of the purified gas continuous-flow interim storage facility 10. Gas from purified gas line 9 flows through the charging valve 50 charging, first, the low-pressure accumulator 47 and then the high-pressure accumulator 48 via the purified-gas compressor 49. At the same time, the output power of the operative module 54 of the methanol synthesis plant 7 is increased. If this is not sufficient to reach equilibrium between the total supply and the gas consumption, further modules 55, 56 of the methanol synthesis plant 7 are set in operation. To this end, hot synthesis exhaust gas of an operative module 54 is introduced via one of the valves 70, 71 opening into the recirculation line 61, 62 of the module to be set in operation, and its synthesis reactor 57, 58 is heated up via the hydrogen enrichment stage 65, 66 and the loop compressor 63, 64. This heating-up takes place in addition to the heating-up via heat exchangers which are associated with the individual modules but are not specifically shown in the drawing. By this double heating, modules 55, 56 can be set in operation at an accelerated rate. As many modules are added successively into the circuit until approximately equilibrium exists again between gas supply and gas consumption.

Complete shut down of the gas turbine leads to a condition in which all modules of the methanol synthesis plant are switched on and together completely take up the amount of purified gas furnished by the coal gasification plant 2. Depending on the design of the methanol synthesis plant 7, this can be that amount of pure gas which is furnished by the coal gasifier 11 at rated load or under somewhat reduced load. With the gas turbine shut down, however, the air separation plant 12 cannot be supplied with compressed air via the air compressor 30 of the gas turbine 28, but must be supplied via the supplemental air compressor 17, 18 assigned to the air decomposition plant. A single controllable supplementary air compressor or also several parallel-connected supplementary air compressors 17, 18 can be used as supplementary air compressor(s). The driving power for the supplementary air compressors is taken from the first and third heat exchanger of the heat exchanger installation 3. Their steam capacity is sufficient to drive the steam turbine 36 and to generate electric energy for the internal consumption of the coal gasification plant 2 as well as of the methanol synthesis plant 7 with the compressors 17, 18, 19, 44, 45, 46, 63, 64 associated therewith. With the gas turbine completely shut down, all the synthesis exhaust gas of the continuous-flow synthesis module 54 is fed into the recirculation lines 61, 62 of the other modules 55, 56.

If, due to increasing power demand, the gas turbine 28 is put in operation again, the unchanged purified-gas supply is initially faced by increased consumption. This leads to a pressure drop in the purified gas supply line 9 below the desired pressure. This, in turn, has the result that the discharge valve 51 of the continuous-flow interim storage plant 10 responds by opening. Then, purified gas flows from the high-pressure accumulator 48 into the purified-gas supply line 9 until the desired pressure is reached again. During this time, the equilibrium between the purified-gas supply and the purified-gas demand is re-established by disconnecting or regulating-down individual modules 55, 56 of the methanol synthesis plant 7. Smaller differences in amounts between the purified-gas supply and purified-gas demand are equalized continuously by the purified-gas continuous-flow interim accumulator 10. With the restarting of the gas turbine 28, compressed air from the air compressor 30 of the gas turbine 28 which is not completely required in the combustion chamber 27 associated with the gas turbine as long as the gas turbine is not operated at full load is available again. This excess amount of air can be fed to the air separation plant 12, and therefore the output of air from the supplementary compressors 17, 18 can be reduced. At the same time, the decreased steam supply from the third heat exchanger 22 is again faced by an additional steam supply from the waste heat boiler 32 of the gas turbine 26 because of the raw gas/-purified gas heat exchanger 21 which is now in operation again. Thereby, the total steam supply is increased, and the output of the steam turbine 36 is increased, and more electric power generated.

Coal gasification to produce raw fuel gas containing CO ahd $H_2$ and the removal of impurities such as $H_2S$ and $SO_2$ from the raw gas to produce purified fuel gas, sometimes called synthesis gas, are well known in the art. Likewise, methanol synthesis from CO and $H_2$ is well known in the art. The same is true of air separation into oxygen and nitrogen.

In the embodiment example, the coal gasification plant 2 was operated at a pressure which corresponds to the pressure needed by the combustion chamber 27 of the gas turbine 28. This pressure is considerably lower than the pressure needed for the operation of the methanol synthesis reactors 57, 58, 67. Therefore, purified gas compressors 44, 45, 46 are required for connecting them. These pure-gas compressors can be saved if the pressure in the coal gasifier is increased accordingly. In this case, however, an expansion turbine must be provided in the pure-gas line 9 ahead of the combustion chamber 27 of the gas turbine. In this expansion turbine, part of the energy can be recovered which is consumed by the compressors preceding the coal gasifier.

The foregoing is a description corresponding, in substance, to German application P 33 19 732.6, dated May 31, 1983, international priority of which is being claimed for the instant application, and which is hereby made part of this application. Any material discrepancies between the foregoing specification and the specification of the aforementioned corresponding German application are to be resolved in favor of the latter.

| LIST OF REFERENCE SYMBOLS | |
|---|---|
| Medium-load power generating plant | 1 |
| Coal gasification plant | 2 |
| Raw-gas heat exchanger installation | 3 |
| Gas purifier | 4 |
| Gas turbine power generating plant part | 5 |
| Steam power generating plant part | 6 |
| Methanol synthesis plant | 7 |
| Pure-gas distribution system | 8 |
| Pure-gas supply line | 9 |
| Pure-gas continuous-flow interim storage plant | 10 |
| Coal gasifier | 11 |
| Air decomposition plant | 12 |
| Buffer accumulator | 13, 14 |
| Oxygen line | 15 |
| Nitrogen line | 16 |
| Supplementary air compressor | 17, 18 |
| Gas compressor | 19 |
| Heat exchanger | 20, 22 |
| Raw-gas/pure-gas heat exchanger | 21 |
| Regulating cooler | 23 |
| Raw-gas scrubber | 24 |
| Hydrogen sulfide absorption plant | 25 |
| Sulfur extraction plant | 26 |
| Combustion chamber | 27 |
| Gas turbine | 28 |
| Generator | 29 |
| Air compressor | 30 |
| Exhaust gas line | 31 |
| Waste heat boiler | 32 |
| Steam line | 33 |
| High-pressure part | 34 |
| Low-pressure part | 35 |
| Steam turbine | 36 |
| Generator | 37 |
| Condenser | 38 |
| Condensate pump | 39 |
| Feedwater tank | 40 |
| Feedwater pump | 41, 42, 43 |
| Pure-gas compressor | 44, 45, 46 |
| Low-pressure accumulator | 47 |
| High-pressure accumulator | 48 |
| Pure-gas compressor | 49 |
| Charging valve | 50 |
| Discharge valve | 51 |
| Mixing section | 52 |
| Mixing chamber | 53 |
| Module | 54, 55, 56 |
| Synthesis reactor | 57, 58 |
| Methanol separator | 59, 60 |
| Recirculation line | 61, 62 |
| Loop compressor | 63, 64 |
| Hydrogen enrichment stage | 65, 66 |
| Synthesis reactor | 67 |
| Methanol separator | 68 |
| Synthesis exhaust gas line | 69 |
| Valve | 70, 71, 72 |
| Valve | 73, 74 |
| Compressor | 75 |

We claim:
1. A medium-load power generating plant with an integrated coal gasification plant comprising
   (a) a coal gasification plant for producing raw hot fuel gas-containing carbon monoxide and hydrogen,
   (b) a raw gas heat exchanger installation having a first raw gas heat exchanger for indirect heat exchange between the hot raw gas from the coal gasification plant with feedwater to generate steam,
   (c) a gas purifier for purifying the raw gas,
   (d) a central purified gas distribution system,
   (e) a purified gas supply line connected to the raw gas heat exchanger installation and passing into the central purified gas distribution system,
   (f) a purified gas continuous-flow interim storage plant connected parallel to the purified gas supply line, wherein the purified gas continuous-flow interim storage plant contains a low-pressure accumulator connected via a charging valve to the purified gas supply line and a high-pressure accumulator connected via a discharge valve to the purified gas supply line, which accumulators are connected to each other via a pressure-increasing compressor for keeping the pressure in the pure-gas supply line constant, as a control and interim storage plant (g) a gas turbine power generating plant connected to the coal gasification plant to receive fuel via the purified gas supply line, (h) a steam power generating plant having a waste heat boiler for generating steam connected to an exhaust line from the gas turbine of the gas turbine power generating plant, a steam turbine connected to the waste heat boiler to receive steam to drive the steam turbine, a generator coupled with the steam turbine to generate electricity, and a condenser, pump and tank for recirculating steam condensate from the steam turbine to the waste heat boiler, (i) a methanol synthesis plant having parallel-connected modules for converting CO and $H_2$ into methanol connected to the gas turbine power generating plant via the central purified gas distribution system.

2. A medium-load power generating plant with an integrated coal gasification plant comprising (a) a coal gasification plant for producing raw hot fuel gas-containing carbon monoxide and hydrogen, (b) a raw gas heat exchanger installation having a first raw gas heat exchanger for indirect heat exchange between the hot raw gas from the coal gasification plant with feedwater to generate steam, wherein the raw gas heat exchanger installation comprises three heat exchangers, of which the first and the third serve for generating steam and the second serves for preheating the purified gas flowing into the combustion chamber of the gas turbine of the gas turbine power generation plant, (c) a gas purifier for purifying the raw gas, (d) a central purified gas distribution system, (e) a purified gas supply line connected to the raw gas heat exchanger installation and passing into the central purified gas distribution system, (f) a purified gas continuous-flow interim storage plant connected parallel to the purified gas supply line, (g) a gas turbine power generating plant connected to the coal gasification plant to receive fuel via the purified gas supply line, (h) a steam power generating plant having a waste heat boiler for generating steam connected to an exhaust line from the gas turbine of the gas turbine power generating plant, a steam turbine connected to the waste heat boiler to receive steam to drive the steam turbine, a generator coupled with the steam turbine to generate electricity, and a condenser, pump and tank for recirculating steam condensate from the steam turbine to the waste heat boiler, (i) a methanol synthesis plant having parallel-connected modules for converting CO and $H_2$ into methanol connected to the gas turbine power generating plant via the central purified gas distribution system.

3. Medium-load power generating plant according to claim 2, wherein the steam power generating plant with the steam turbine coupled to an electric generator are connected to the first and third heat exchangers for supplying at least part of the steam for driving the steam turbine, and wherein the heat exchange surfaces of the first and third heat exchangers are sufficient, with the gas turbine of the gas turbine power plant shut down and the coal gasification plant running, to extract adequate heat from the raw gas passing through said heat exchangers to generate steam to drive the steam turbine and maintain the internal electric supply of the coal gasification plant and of the methanol synthesis plant.

4. Medium-load power-generating plant according to claim 2, wherein the third heat exchanger is provided with adequate heating surface to take up the raw gas heat which is additionally produced under partial load or shutdown of the gas turbine.

5. Medium-load power-generating plant according to claim 3, wherein the third heat exchanger is provided with adequate heating surface to take up the raw gas heat which is additionally produced under partial load or shutdown of the gas turbine.

6. A medium-load power generating plant with an integrated coal gasification plant comprising (a) a coal gasification plant for producing raw hot fuel gas-containing carbon monoxide and hydrogen, (b) a raw gas heat exchanger installation having a first raw gas heat exchanger for indirect heat exchange between the hot raw gas from the coal gasification plant with feedwater to generate steam, (c) a gas purifier for purifying the raw gas, (d) a central purified gas distribution system, (e) a purified gas supply line connected to the raw gas heat exchanger installation and passing into the central purified gas distribution system, (f) a purified gas continuous-flow interim storage plant connected parallel to the purified gas supply line, (g) a gas turbine power generating plant connected to the coal gasification plant to receive fuel via the purified gas supply line, (h) a steam power generating plant having a waste heat boiler for generating steam connected to an exhaust line from the gas turbine of the gas turbine power generating plant, a steam turbine connected to the waste heat boiler to receive steam to drive the steam turbine, a generator coupled with the steam turbine to generate electricity, and a condenser, pump and tank for recirculating steam condensate from the steam turbine to the waste heat boiler, (i) a methanol synthesis plant having parallel-connected modules for converting CO and $H_2$ into methanol connected to the gas turbine power generating plant via the central purified gas distribution system, wherein the not completely reacted synthesis exhaust gas of at least one of the modules of the methanol synthesis plant can be returned by means of a loop compressor via a hydrogen enrichment stage into a methanol synthesis reactor.

7. A medium-load power generating plant with an integrated coal gasification plant comprising (a) a coal gasification plant for producing raw hot fuel gas-containing carbon monoxide and hydrogen, (b) a raw gas heat exchanger installation having a first raw gas heat exchanger for indirect heat exchange between the hot raw gas from the coal gasification plant with feedwater to generate steam, (c) a gas purifier for purifying the raw gas, (d) a central purified gas distribution system, (e) a purified gas supply line connected to the raw gas heat exchanger installation and passing into the central purified gas distribution system, (f) a purified gas continuous-flow interim storage plant connected parallel to the purified gas supply line, (g) a gas turbine power generating plant connected to the coal gasification plant to receive fuel via the purified gas supply line, (h) a steam power generating plant having a waste heat boiler for generating steam connected to an exhaust line from the gas turbine of the gas turbine power generating plant, a steam turbine connected to the waste heat boiler to receive steam to drive the steam turbine, a generator coupled with the steam turbine to generate electricity, and a condenser, pump and tank for recirculating steam condensate from the steam turbine to the waste heat boiler, (i) a methanol synthesis plant having parallel-connected modules for converting CO and $H_2$ into methanol connected to the gas turbine power generating plant via the central purified gas distribution system, and (j) a mixing section into which the synthesis gas which is not fully reacted in a synthesis reactor of at least one module of the methanol synthesis plant can be fed to the purified gas supply line leading to the gas turbine power-generating plant part.

8. Medium-load power-generating plant according to claim 6, including connecting means for feeding the not completely reacted synthesis exhaust gas of at least one module of the methanol synthesis plant into a recirculation line leading back to a synthesis reactor of the other modules to accelerate the starting thereof.

9. Medium-load power-generating plant according to claim 7, including connecting means for feeding the not completely reacted synthesis exhaust gas of at least one module of the methanol synthesis plant into a recirculation line leading back to a synthesis reactor of the other modules to accelerate the starting thereof.

10. A medium-load power generating plant with an integrated coal gasification plant comprising (a) a coal gasification plant for producing raw hot fuel gas-containing carbon monoxide and hydrogen, (b) a raw gas heat exchanger installation having a first raw gas heat exchanger for indirect heat exchange between the hot raw gas from the coal gasification plant with feedwater to generate steam, (c) a gas purifier for purifying the raw gas, (d) a central purified gas distribution system, (e) a purified gas supply line connected to the raw gas heat exchanger installation and passing into the central purified gas distribution system, (f) a purified gas continuous-flow interim storage plant connected parallel to the purified gas supply line, (g) a gas turbine power generating plant connected to the coal gasification plant to receive fuel via the purified gas supply line, (h) a steam power generating plant having a waste heat boiler for generating steam connected to an exhaust line from the gas turbine of the gas turbine power generating plant, a steam turbine connected to the waste heat boiler to receive steam to drive the steam turbine, a generator coupled with the steam turbine to generate electricity, and a condenser, pump and tank for recirculating steam condensate from the steam turbine to the waste heat boiler, (i) a methanol synthesis plant having parallel-connected modules for converting CO and $H_2$ into methanol connected to the gas turbine power generating plant via the central purified gas distribution system, and (j) a bleed line from a recirculation line of a module of the methanol synthesis plant for the passage of synthesis exhaust gas to a steam generator wherein the exhaust gas is burned and steam generated by the heat of combustion.

11. Medium-load power-generating plant according to claim 6, including a bleed line from a recirculation line of a module of the methanol synthesis plant for the passage of synthesis exhaust gas to a steam generator wherein the exhaust gas is burned and steam generated by the heat of combustion.

12. A medium-load power generating plant with an integrated coal gasification plant comprising (a) a coal gasification plant for producing raw hot fuel gas-containing carbon monoxide and hydrogen, (b) a raw gas heat exchanger installation having a first raw gas heat exchanger for indirect heat exchange between the hot raw gas from the coal gasification plant with feedwater to generate steam, (c) a gas purifier for purifying the raw gas, (d) a central purified gas distribution system, (e) a purified gas supply line connected to the raw gas heat exchanger installation and passing into the central purified gas distribution system, (f) a purified gas continuous-flow interim storage plant connected parallel to the purified gas supply line, (g) a gas turbine power generating plant connected to the coal gasification plant to receive fuel via the purified gas supply line, including a second gas turbine coupled with a generator in addition to the gas turbine and generator of the gas turbine generating power plant for supplying the internal electric energy requirements by burning residual gas, largely reacted by recirculation, from the individual modules of the methanol synthesis plant, (h) a steam power generating plant having a waste heat boiler for generating steam connected to an exhaust line from the gas turbine of the gas turbine power generating plant, a steam turbine connected to the waste heat boiler to receive steam to drive the steam turbine, a generator coupled with the steam turbine to generate electricity, and a condenser, pump and tank for recirculating steam condensate from the steam turbine to the waste heat boiler, (i) a methanol synthesis plant having parallel-connected modules for converting CO and $H_2$ into methanol connected to the gas turbine power generating plant via the central purified gas distribution system.

13. Medium-load power-generating plant according to claim 6, including a second gas turbine coupled with a generator in addition to the gas turbine and generator of the gas turbine generating power plant, for supplying the internal electric energy requirements by burning residual gas, largely reacted by recirculation, from the individual modules of the methanol synthesis plant.

14. Medium-load power-generating plant according to claim 2, including a water-cooled regulating cooler for keeping the raw-gas output temperature of the raw-gas heat exchanger installation constant.

15. A medium-load power generating plant with an integrated coal gasification plant comprising
   (a) a coal gasification plant for producing raw hot fuel gas-containing carbon monoxide and hydrogen,
   (b) a raw gas heat exchanger installation having a first raw gas heat exchanger for indirect heat exchange between the hot raw gas from the coal gasification plant with feedwater to generate steam,
   (c) a gas purifier for purifying the raw gas,
   (d) a central purified gas distribution system,
   (e) a purified gas supply line connected to the raw gas heat exchanger installation and passing into the central purified gas distribution system,
   (f) a purified gas continuous-flow interim storage plant connected parallel to the purified gas supply line,
   (g) a gas turbine power generating plant connected to the coal gasification plant to receive fuel via the purified gas supply line,
   (h) a first air compressor connected to supply air to the gas-turbine power generating plant and an air-separation plant associated with the coal gasifier, at least one additional air compressor which is connected parallel to the first air compressor and by which the supply of the air to the air-separation plant preceding the coal gasifier can be supplemented,
   (i) a steam power generating plant havng a waste heat boiler for generating steam connected to an exhaust line from the gas turbine of the gas turbine power generating plant, a steam turbine connected to the waste heat boiler to receive steam to drive the steam turbine, a generator coupled with the steam turbine to generate electricity, and a condenser, pump and tank for recirculating steam condensate from the steam turbine to the waste heat boiler,
   (j) a methanol synthesis plant having parallel-connected modules for converting CO and $H_2$ into methanol connected to the gas turbine power generating plant via the central purified gas distribution system.

16. Medium-load power generating plant according to claim 15, including means for activating the additional air compressor to supply air to the coal gasifier plant for operating the methanol synthesis plant when the gas turbine power generating plant shuts down.

* * * * *